(12) United States Patent
Rzany et al.

(10) Patent No.: US 11,298,225 B2
(45) Date of Patent: Apr. 12, 2022

(54) MEDICAL IMPLANT WITH SEAMLESSLY CONNECTED BACTERIAL CELLULOSE

(71) Applicant: BIOTRONIK AG, Buelach (CH)

(72) Inventors: Alexander Rzany, Nuremberg (DE); Tina Pieger, Rohr (DE); Bernhard Hensel, Erlangen (DE)

(73) Assignee: BIOTRONIK AG, Buelach (CH)

( * ) Notice: Subject to any disclaimer, the term of this patent is extended or adjusted under 35 U.S.C. 154(b) by 0 days.

(21) Appl. No.: 16/387,724

(22) Filed: Apr. 18, 2019

(65) Prior Publication Data

US 2019/0358031 A1    Nov. 28, 2019

(30) Foreign Application Priority Data

May 23, 2018  (EP) .................... 18173849

(51) Int. Cl.
| | |
|---|---|
| *A61F 2/24* | (2006.01) |
| *A61F 2/06* | (2013.01) |
| *A61L 31/04* | (2006.01) |
| *A61L 31/14* | (2006.01) |
| *A61L 27/50* | (2006.01) |

(52) U.S. Cl.
CPC .............. *A61F 2/2415* (2013.01); *A61F 2/06* (2013.01); *A61F 2/2409* (2013.01); *A61F 2/2412* (2013.01); *A61F 2/2463* (2013.01); *A61L 31/042* (2013.01); *A61L 31/14* (2013.01); *A61F 2/2475* (2013.01); *A61L 27/507* (2013.01)

(58) Field of Classification Search
None
See application file for complete search history.

(56) References Cited

U.S. PATENT DOCUMENTS 4,588,400 A    5/1986   Ring et al.

FOREIGN PATENT DOCUMENTS

| | | |
|---|---|---|
| DE | 4027479 A1 | 3/1991 |
| EP | 1660670 A1 | 5/2006 |
| WO | 2005003366 A1 | 1/2005 |
| WO | 2013119912 A1 | 8/2013 |
| WO | 2016083351 A1 | 6/2016 |
| WO | WO-2016083351 A  * | 6/2016 ........... A61L 27/507 |

OTHER PUBLICATIONS

Jia et al., "Preparation and Characterization of Bacterial Cellulose Tube", 2009—3rd International Conference on Bioinformatics and Biomedical Engineering, DOI:10.1109/ICBBE.2009.5163226, pp. 1-4.

* cited by examiner

*Primary Examiner* — Leslie Lopez
(74) *Attorney, Agent, or Firm* — Laurence A. Greenberg; Werner H. Stemer; Ralph E. Locher

(57) ABSTRACT

An implant has a support structure (e.g., alloplastic) such as a stent or a scaffold, and a functional element (e.g., a heart valve) including or made of bacterial cellulose. At least a part of the support structure is embedded in the functional element or in an extension thereof so as to connect the functional element to the structural element via positive fit.

9 Claims, 3 Drawing Sheets

MEDICAL IMPLANT WITH SEAMLESSLY CONNECTED BACTERIAL CELLULOSE

CROSS-REFERENCE TO RELATED APPLICATION

This application claims the priority, under 35 U.S.C. § 119, of European application EP 18173849.3, filed May 23, 2018; the prior application is herewith incorporated by reference in its entirety.

BACKGROUND OF THE INVENTION

Field of the Invention

The present invention relates to an implant to be implanted into a body of a patient and also to a method for producing such an implant.

In general, sutures are required to make implants having biological tissue parts. These allow connecting the tissue part to a support structure or scaffold of the implant and/or for achieving a three-dimensional form of the respective tissue part.

Surgical sutures normally have to be positioned manually, which constitutes an involved and expensive process that is also prone to human error. Furthermore, knots have to be individually checked visually. Furthermore, each knot represents a potential weak point of the implant, particularly due to the fact that forces arising between biological material and the structural scaffold are focused on the knots. Furthermore, surgical sutures have a certain space requirement that cannot be neglected, which means that the minimal size of implants that can be produced this way is in the order of a few millimeters in any given dimension.

BRIEF SUMMARY OF THE INVENTION

Therefore it is an objective of the present invention to provide an implant and a method for producing such an implant that is improved regarding the above described difficulties.

With the above and other objects in view there is provided, in accordance with the invention, an implant, comprising:

a support structure having a three-dimensional shape; and a functional element having a three-dimensional shape deviating, at least in part, from the three-dimensional shape of said support structure;

wherein a part of said support structure is embedded in a part of said functional element that comprises bacterial cellulose so as to connect said functional element to said support structure.

In other words, the above and other objects are achieved with an implant that implant that includes a support structure (e.g., an alloplastic structure such as a stent or a scaffold), and a functional element. The three-dimensional shape of the functional element at least in part deviates from the three-dimensional shape of the support structure, and a part of the support structure is embedded in a part of the functional element that comprises bacterial cellulose so as to connect the functional element to the support structure.

According to the present invention at least a part of the support structure is embedded in a part of the functional element or in an extension thereof so as to connect the functional element to the support structure. Particularly, the functional element is connected to the support structure in a sutureless (seamless) fashion. A part of the three-dimensional shape of the functional element deviates from the three-dimensional shape of the support element. The support element is not embedded in the part of the functional element that deviates from the support structure. As a result, this part of the functional element is free to move independently from the support structure and is therefore able to perform a physiological function. This is important for example for a heart valve implant in which at least part of the functional element, the heart valve element, has to be able to flexibly open and close in response to blood flow. Preferably, at least 10% of the three-dimensional shape of the functional element deviates from the support structure, more preferably at least 20%, even more preferably at least 30%, yet more preferably at least 40% and most preferably at least 50%. The larger the part of the functional element that deviates from the support structure, the more of the functional element surface area can be used by the implant to perform a function that necessitates a movement of the functional element that is independent of that of the support structure.

In accordance with a preferred implementation, the functional element comprises at least a part that is substantially made of bacterial cellulose. This part of the functional element preferably has a part of the support structure embedded within so as to connect the functional element to the support structure.

An object that is substantially, or essentially, made of bacterial cellulose in the context of this disclosure refers to an object that is made by deposition of bacterial cellulose on a given surface by a bacterium that produces bacterial cellulose.

Such bacterial cellulose is usually of high purity and therefore the thus formed object essentially consists of bacterial cellulose. Bacterial cellulose that contains impurities or for example cellular debris from bacteria or entire bacteria that were incorporated during the deposition of the bacterial cellulose by the bacteria would still be counted in the context of this disclosure as bacterial cellulose that is substantially made of, or essentially consists of, bacterial cellulose.

The part of the functional element that is not supported by the support element and the part which is supported by the support element are preferably integrally made of a single piece. In other words, the part of the functional element that deviates from the support element and the part of the functional element into which a part of the structural element is embedded (or the extension of the functional element into which a part of the structural element is embedded) are preferably integrally made of a single piece. This greatly facilitates the production of such implants. Preferably, the entire functional element (with possible extension) essentially consists of bacterial cellulose and is preferably made of a single piece of bacterial cellulose. It should be noted that a single piece of bacterial cellulose can be made in several growing steps. A piece of bacterial cellulose resulting from extending or thickening (by deposition of further bacterial cellulose by bacteria) a first piece of bacterial cellulose is to be considered a single piece of bacterial cellulose.

Thus, the solution according to the present invention allows omitting surgical sutures as a fastening means for fastening functional elements to the structural bodies/scaffolds (i.e., the support structures). Furthermore, this allows to drastically simplify a manufacturing process for manufacturing an implant according to the present invention. Particularly, implants can be provided that have sophisticated functional element(s) connected in a simple sutureless manner to an underlying structural body/support structure.

The functional element of an implant is an element that, in essence, carries out a function of the implant. For example, in the case of a heart valve prosthesis, a functional element comprises a heart valve element. The heart valve element is adapted to close in response to retrograde blood flow and to open in response to antegrade blood flow. It therefore carries out the function of the heart valve, which is to prevent retrograde blood flow (in the direction opposite to the intended direction). In order to carry out its function, the heart valve element (or parts of it) needs to be able to move independently of the support structure. The heart valve element itself that allows the heart valve implant to carry out its function therefore deviates from the rigid support structure so as to carry out its function. A part of the support structure can, where appropriate, be embedded in a part of the functional element itself. However, the functional element may also have an extension into which the support structure is embedded. In the case of the heart valve prosthesis, one such extension may for example be a skirt that extends along the stent, preferably in the retrograde direction starting from the heart valve element. Such an extension is however also part of the functional element of the implant, since the skirt and the heart valve element are integrally formed. In the context of this disclosure, the functional element is therefore not to be interpreted in its narrow sense but encompasses all the elements directly attached to (integrally formed with) the functional element per se. In the case of the heart valve prosthesis therefore, the functional element is to be understood as the heart valve element itself and at least the skirt when the two elements are formed as a single body.

Furthermore, according to a preferred embodiment of the implant according to the present invention, the functional element is entirely made of bacterial cellulose, and preferably the functional element is made of a single piece of bacterial cellulose that does not comprise any seams. This is achieved by growing the entire functional element on a mold, or on several molds, as described further below. Alternatively, in an embodiment, only a part of the functional element in which said part of the support structure is embedded, is essentially made of bacterial cellulose.

Furthermore, according to an embodiment of the implant according to the present invention, the functional element forms a three-dimensional body.

Further, in an embodiment, the functional element is selected from the following group: a vascular patch, an occluder, an artificial tendon, a venous valve, a sealing member, particularly for preventing a paravalvular leakage, e.g. in case the implant is a heart valve prosthesis, see also below.

Furthermore, according to an embodiment of the implant according to the present invention, the support structure has a generally cylindrical shape and a lumen that extends through the support structure. Such structures are particularly appropriate for the types of implants of the present invention because a functional three-dimensional element with a complex structure can particularly easily be attached to such a structure, and particularly inside such a structure.

Furthermore, according to an embodiment of the implant according to the present invention, the support structure is a stent.

According to a further embodiment of the implant according to the present invention, the stent comprises a plurality of struts connected to each other so that the stent comprises a plurality of cells which form recesses of the support structure via which a first side (e.g. an inside of the stent) is connected to a second side (e.g. an outside) of the stent. In the implanted state the outside faces a vascular wall.

According to a further embodiment of the implant according to the present invention, a plurality of struts of the stent are embedded into the functional element so that the functional element encloses these struts (at least in a cross-sectional plane running perpendicular to the respective strut).

Furthermore, according to an embodiment, the stent is embedded in the functional element/tissue element such that a plurality of cells of the stent are completely embedded into the functional element, so that the functional element fills the respective cell and forms a closed wall section in a peripheral direction of the stent (e.g. a skirt). This leads to a particularly strong attachment of the functional element to the support structure and therefore allows the implant to withstand high mechanical load.

Particularly, the stent can be a self-expanding stent formed out of a suitable metal such as a nickel titanium alloy (e.g., Nitinol) or a stent that is configured to be expanded by means of an inflatable balloon of a balloon catheter which is configured to exert a force on the stent so that the latter expands from a crimped or collapsed state into an expanded state.

Particularly, according to an embodiment of the present invention, the part of the functional element that does not comprise an embedded support structure (i.e., the part of the functional element that deviates from the support structure) is configured to be able to move freely with respect to the support structure in an implanted state of the implant. As an example of such an embodiment, the heart valve element of the heart valve prosthesis comprises a first part into which a part of the support structure is embedded and a second part (the heart valve leaflets) that is able to move relative to the support structure while still being anchored to the support structure.

Furthermore, in an embodiment, in case the support structure is a stent, at least a part of the functional element can at least partially coat the stent.

Furthermore, in an embodiment, the support structure comprises, or consists of, a sponge-like and or mesh structure. Such a support structure, or part of a support structure, can also be at least partially embedded into the bacterial cellulose of the functional element. An example of such an embodiment would be a heart valve prosthesis with a sponge-like polymer structure or a biological collagen sponge in the area of the skirt. This sponge-like structure can be configured to prevent paravalvular leakage by sealing the space between the stent of the heart valve prosthesis and the natural cavity into which the prosthesis is inserted. The sealing effect of this sponge-like structure is strengthened by added bacterial cellulose into which it is embedded.

Furthermore, in an embodiment, the functional element that deviates from the first support structure can comprise a second support structure embedded within it. This part of the functional element is still free to move relative to the first support structure. In one embodiment, the second support structure is a polymer network which is optionally embedded into the bacterial cellulose of the functional element that deviates from the first support structure.

Furthermore, according to an embodiment of the implant according to the present invention, the implant is a heart valve prosthesis, particularly an aortic heart valve prosthesis or a mitral heart valve prosthesis.

Furthermore, according to an embodiment of the implant according to the present invention, the functional element comprises a skirt of the heart valve prosthesis, wherein particularly a circumferential section of the stent is embedded into the skirt formed by this part of the functional element.

Furthermore, according to an embodiment of the implant according to the present invention, the functional element forms one of: at least one valve leaflet, a plurality of valve leaflets, three valve leaflets. Particularly, said valve leaflets formed by the functional element are integrally (seamlessly) connected to one another.

Furthermore, according to an embodiment of the implant according to the present invention, at least one valve leaflet or said plurality of valve leaflets are integrally connected to said skirt formed by the functional element. Thus, in a heart valve prosthesis, the functional element can form a single functional element of the prosthesis that comprises the valve leaflets and the skirt in an integral fashion. The skirt can serve as a sealing member which in some embodiments allows preventing paravalvular leakage. The advantage of such an implant is that it is much easier and cheaper to produce than an implant that comprises the different leaflets and the skirt all made of distinct pieces that have to be sewn together. This skirt in such an implant serves the double function of attaching (or further attaching) the heart valve element to the stent and of preventing paravalvular leakage.

Furthermore, according to an embodiment of the implant according to the present invention, the implant or heart valve prosthesis is configured to be implanted into a patient via a catheter device, wherein particularly the heart valve prosthesis is an aortic heart valve prosthesis that is particularly configured to be implanted by means of TAVI (Transcatheter Aortic Valve Implantation). In an alternative embodiment, the implant or heart valve prosthesis is configured to be implanted via surgery.

Furthermore, in an embodiment, the skirt forms a sealing member for preventing paravalvular leakage.

In one embodiment, the functional element comprises areas of different bacterial cellulose thicknesses. It can be advantageous to vary the thickness of the bacterial cellulose of the functional element for various reasons. The functional element made of cellulose can adopt any 3D-shape as required by its function. A thicker bacterial cellulose layer can provide higher mechanical resistance to areas of the functional element on which the mechanical load in the implanted state is particularly strong. Conversely, areas of the functional element that should be particularly flexible can be made thinner. This can for example be the case for the ends of the heart valve leaflets which have to be particularly mobile in the implanted state in order to minimize blood flow disruption.

In one embodiment, the functional element of the implant comprises fine structures on its surface that mimic, or improve on, the structures on the biological element that the functional element (or part of the functional element) is meant to replace. Such structures can for example in the case of a heart valve implant be thicker portions of the valve leaflets that are particularly exposed to mechanical stress when implanted. This has the clear advantage that the implant would be less prone to degradation. Another type of structures that can be made on the surface for example of the heart valve leaflets are striations in the direction of blood flow to facilitate blood flow. Such structures can be obtained during the production of the implant by varying the thickness of the oxygen-permeable mold used for the production of the functional element. The thicker the mold in a given position, the less oxygen is able to diffuse through this position and the thinner will be the bacterial cellulose in the corresponding position in the functional element. It is therefore possible to obtain fine structures in the functional element by varying the corresponding thickness or surface structure of the mold used for the production of the functional element.

With the above and other objects in view there is provided, in accordance with the invention, a method of producing an implant, particularly an implant as described herein, with a support structure and a functional element comprising the steps of:
  a) providing a support structure,
  b) providing a three-dimensional mold of the functional element,
  c) positioning the mold relative to the support structure, and
  d) placing the mold and the support structure under conditions conducive to growing bacterial cellulose on and/or in the mold so as to form the functional element and so as to embed at least a part of the support structure in at least a part of the functional element, thereby connecting the functional element to the support structure,
  e) optionally washing the bacterial cellulose,
  f) optionally drying the bacterial cellulose,
  wherein the three-dimensional shape of the functional element at least in part deviates from the three-dimensional shape of the support structure.

Positioning the mold relative to the support structure in step c) essentially means positioning the mold relative to the support structure in such a way that when bacterial cellulose is deposited on the inner surface, on the outer surface or on both surfaces of the mold by bacteria, the functional element is mechanically connected to the support structure by positive fit, as intended. In practice this generally means that at least one portion of the mold faces at least one portion of the support structure at a distance that is small enough to be filled by growing (depositing) bacterial cellulose on the mold and in some embodiments also on the support structure.

The three-dimensional mold of the functional element is preferably made of an oxygen-permeable material such as silicone. This allows growing the bacterial cellulose in a targeted way only where oxygen is provided to the bacteria through the permeable material.

Bacterial cellulose is an extracellular metabolic product formed by microorganisms. As a result, many of its properties are comparable to those of cellulose of plant origin. However, its purity is significantly higher, since it contains no foreign polymers or other inclusions. The supermolecular structure of bacterial cellulose makes it very hydrophilic and gives it high absorptivity and mechanical strength. For synthesis of cellulose, both gram-negative microorganisms (*Gluconacetobacter* (*G.*), *Azotobacter, Rhizobium, Pseudomonas, Salmonella, Alcaligenes*) and gram-positive ones (*Sarcina ventriculi*) can be used. The most frequently used of these are *G. xylinus, G. hansenii*, and *G. pasteurianus*. For this invention, the gram-negative aerobic species *Gluconacetobacter xylinus* (also called *Acetobacter xylinum*) is especially preferred.

The bacterial cellulose in the hybrid material system (support structure and functional element) can optionally be reduced in thickness in a subsequent process step by air drying or drying at elevated temperature, for example in a heating cabinet. Preferably the air drying step is performed at least partially at a temperature from between room temperature (around 20° C.) and 80° C., more preferably between 40° C. and 70° C. and most preferably at 60° C. After drying, the bacterial cellulose is practically non-swellable and permanently dimensionally stable, while retaining its form-fit with the alloplastic support structure. In order to obtain a swellable bacterial cellulose, it can be conserved by structure-stabilizing substances before drying, similar to the processes in dry conserved pericardium. Such a process is for example disclosed in patent application publication No. US 2015/0282930 A1 and its counterpart European published patent application EP 2 926 840 A1 and can comprise a step of treating the bacterial cellulose with solutions comprising glycerol and/or polyethylene glycol. This step is preferably performed before the optional drying step f).

In one embodiment, the method further comprises a step of removing the mold after step d) and further growing the bacterial cellulose in the absence of the first mold. This further step leads to the deposition of additional bacterial cellulose and in turn leads to a functional element with a thicker or denser bacterial cellulose layer than could be obtained while growing the bacterial cellulose on the mold. An advantage of a thicker bacterial cellulose layer an implant that can withstand higher mechanical loads is provided. This further step therefore also allows extending the functional life time of the implant.

It is also possible to further grow the bacterial cellulose layer in this step in only parts of the implant, for example by specifically applying medium to only the parts of the functional elements where bacterial cellulose is to be further grown. It is for example possible to specifically further grow bacterial cellulose only on the part of the functional element into which a part of the support structure is embedded. As a result, the mechanical connection between the functional element and the support structure will be increased without increasing the layer thickness of the rest of the functional element. The resulting implant has a stronger mechanical connection between the functional element and the support structure while at the same time having a highly flexible part of the functional element that deviate from the support structure, since the thickness of this part of the functional element is not increased. Alternatively the thickness of only the part of the functional element that deviates from the support structure can be increased or the thickness of the entire functional element.

This step can be performed by (selectively) applying further growth medium to a functional element grown on a first mold (for example by dipping). Optionally, this further step is performed in the presence of a second mold, which can further shape the functional element by targeted further growth of bacterial cellulose on specific sections of the functional element (see further details below).

In accordance with an added feature of the invention, the bacterial cellulose is grown by incubating the support structure and the mold in a medium comprising a bacterial cellulose-producing bacterium, preferably *Acetobacter xylinum*.

In accordance with a further feature of the invention, the method comprises the additional steps of providing a further mold, preferably made of an oxygen-permeable material, and producing a further element comprising, or essentially made of, bacterial cellulose. The second element can be independent of the functional element or can be grown to converge with the functional element. In the latter case, the functional element and the second element join together and are to be seen as a single functional element. This extended functional element comprises at least a functional part and can comprise a further part that serves to (further) attach the functional element to the support structure. The second element can however also have an additional function of its own, that may be independent of the first function of the functional element. A practical example of such an implant is for example a heart valve prosthesis. The functional element is the heart valve element itself and the second element is a skirt that not only allows to further attach the functional element to the support structure (the stent) but can also have the additional function of preventing paravalvular leakage in the implanted state by extending radially outwards of the stent and optionally being swellable. By extending radially outwards, the skirt fills the gaps between the implant and the vascular element into which it is placed. Such gaps are for example often caused by irregularities on the vascular surface. By filling these gaps, the skirt prevents blood from flowing between the implant and the vascular surface.

One aspect of the present invention relates to a method for producing an implant, particularly an implant as described herein, comprising a support structure and a functional element comprising bacterial cellulose, wherein the functional element is produced and connected to the support structure by growing bacterial cellulose (allowing bacteria to deposit bacterial cellulose) of the functional element on the support structure so that at least a part of the support structure is embedded in the bacterial cellulose of the functional element to connect the functional element to the support structure.

Further, in an embodiment of this method, for growing bacterial cellulose of the functional element on a first side of the support structure at least a first mold is provided and the support structure and at least one first mold are arranged with respect to each other such that a surface of the first mold faces the first side of the support structure and a nutrient solution comprising bacteria producing said bacterial cellulose is applied between said surface and the first side of the support structure such that bacterial cellulose grows from the surface towards the first side of the support structure. An example of a suitable nutrient solution will be described below.

Particularly the first mold is permeable for oxygen. Thus, the bacterial cellulose will particularly grow starting at the surface and from there towards the support structure that is arranged in front of said surface of the mold.

Further, in an embodiment of the method according to the present invention, the support structure comprises recesses connecting the first side of the support structure with a second side of the support structure, wherein the bacterial cellulose is let to grow through the recesses and from there on the second side of the support structure to form the functional element so that the support structure is at least partially embedded in the bacterial cellulose of the functional element, wherein particularly the bacterial cellulose covers the first and the second side of the support structure at least partially (particularly, the support structure can be a stent and said recesses can be cells defined by the struts of the stent, see also below).

Hereafter, the support structure can be removed from first mold and particularly the remaining nutrient solution can be removed from the support structure and/or from the functional element/bacterial cellulose. Particularly, the implant comprising the support structure and the functional element connected thereto can be cleaned. This cleaning can be performed by a washing step.

However, the stent can also be further processed (e.g. after removal of the first mold) by contacting an inside of the grown bacterial cellulose with the nutrient solution and/or by contacting an outer surface of the grown bacterial cellulose with the nutrient solution in order to grow further bacterial cellulose and to therewith form the functional element. This allows growing a thicker layer of bacterial cellulose, which could not be obtained solely by growing the bacterial cellulose on the mold as after a certain thickness, the bacterial cellulose becomes impermeable to oxygen and therefore hinders further growth of the bacterial cellulose layer. This further growth allows strengthening the mechanical attachment of the functional element to the support structure by increasing the thickness of the bacterial cellulose at least of the part of the functional element into which a part of the support structure is embedded. In addition, or as an alternative, it allows increasing the thickness of the bacterial cellulose layer of the functional element part that deviates from the support structure. An increased thickness of the bacterial cellulose layer leads to the implant being able to withstand higher mechanical loads when implanted and therefore extending its lifetime.

Further, according to an alternative embodiment the thickness of the bacterial cellulose of the functional element can also be increased by using a further mold in this step. Particularly, the support structure is removed from the first mold (and particularly the remaining nutrient solution is removed from the support structure and/or from the bacterial cellulose grown thereon), and the support structure and a second mold are arranged with respect to each other such that a surface of the second mold faces a second side of the support structure and a nutrient solution comprising bacteria producing said bacterial cellulose is applied between said surface of the second mold and the second side of the support structure such that bacterial cellulose grows from the surface of the second mold towards the second side of the support structure such that the support structure is at least partially embedded in the bacterial cellulose of the functional element.

Furthermore, in the above embodiments of the method according to the present invention, the support structure is a stent, wherein the first side is an outside of the stent and the second side is an inside of the stent. Alternatively, the first side is an inside of the stent and the second side is an outside of the stent.

Further, in an embodiment of the method according to the present invention, the nutrient solution comprises *Acetobacter xylinum* and/or another suitable bacterium.

Particularly, as described above, the produced implant can be a heart valve prosthesis for replacing a native heart valve, particularly an aortic heart valve, wherein the functional element comprises at least one valve leaflet, a plurality of valve leaflets, or three valve leaflets.

Furthermore, in addition or alternatively, the functional element can comprise a skirt. In an embodiment the skirt is integrally connected to the valve leaflet(s). Furthermore, in an embodiment, the skirt forms a sealing member for preventing a paravalvular leakage.

Yet another aspect of the present invention relates to an implant produced by the method according to the present invention.

Advantageously, for the implants according to the present invention, surgical sutures or separate functional elements are no longer needed, such that sutures representing weak points can be omitted and the manufacturing costs can be significantly reduced.

The method according to the invention allows making new types of implants that are too small to be made by traditional methods that involve suturing functional elements onto a support structure. Indeed, with the present method such small elements can be seamlessly attached to the support structure. This allows the realisation of novel implants for small vascular diameters, e.g. venous valves.

The form-fitting connection between the functional element and the support structure also allows an integrated solution for sealing leakages outside the implant, since the functional element can comprise a skirt of a heart valve prosthesis for contacting an annulus region of the native heart valve (see also above).

Furthermore, bacterial cellulose has potential advantages with respect to usual xenogenic materials like porcine pericardium regarding calcification, homogeneity of the material properties, smaller thickness with comparable mechanical properties, possible shapes, stability regarding biological decomposition without additional chemical fixation.

A further aspect of the invention relates to a catheter comprising a heart valve prosthesis with a functional element made of bacterial cellulose which was made by the method of the invention. The heart valve prosthesis is preferably mounted on the catheter in the dried state. This allows providing the heart valve prosthesis to the hospital or clinic where the implantation will be performed in a dried state and the prosthesis does not have to be again mounted on the catheter before implantation.

Other features which are considered as characteristic for the invention are set forth in the appended claims.

Although the invention is illustrated and described herein as embodied in a medical implant with seamlessly connected bacterial cellulose, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 2:
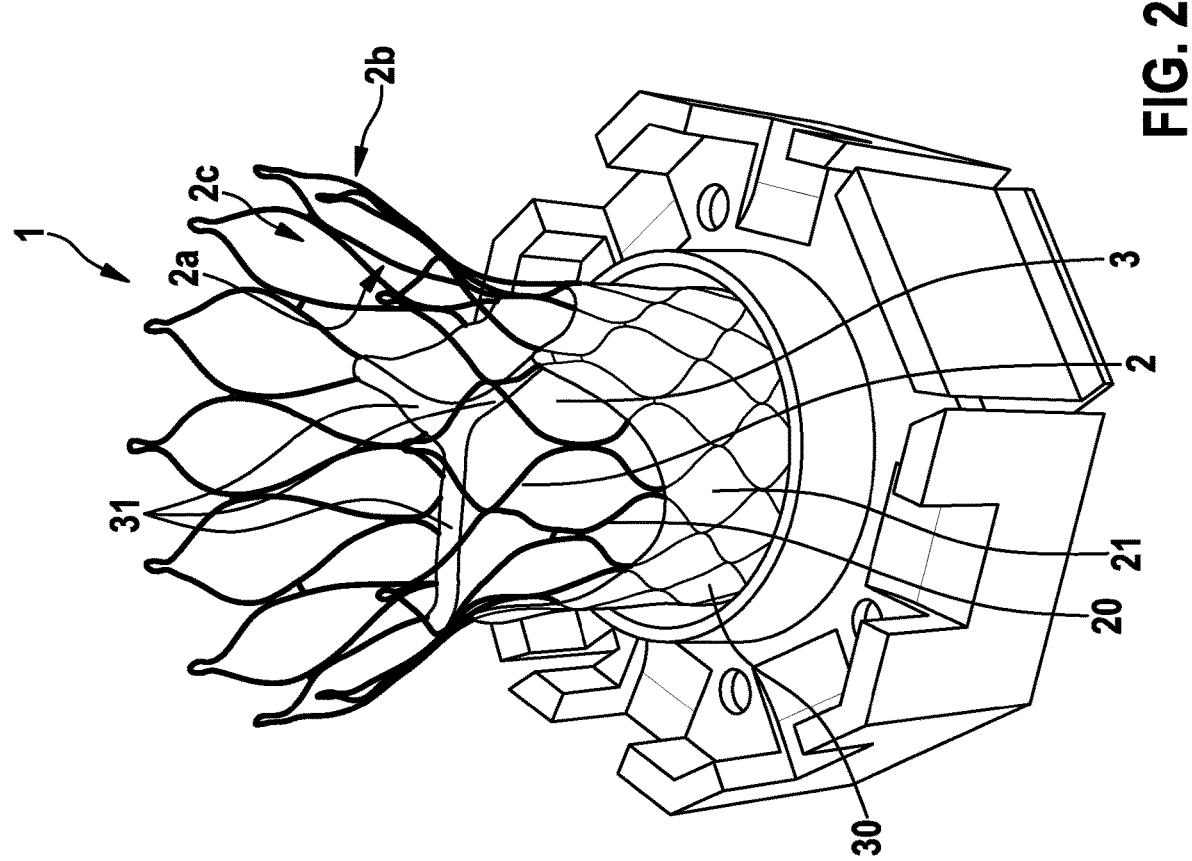
FIG. 2 shows an implant according to the present invention in the form of a heart valve prosthesis.

Referring now to the figures of the drawing in detail and first, particularly, to FIG. 2 thereof, there is shown a perspective view of an embodiment of an implant 1 according to the present invention. The implant 1 comprises a structural (e.g. alloplastic) body, here particularly in the form of a stent 2, and a functional element made of bacterial cellulose. In the present exemplary embodiment, the functional element comprises three valve leaflets 31 that are integrally connected to a skirt 30 of the stent 2. The stent 2 comprises struts 20 that enclose/define cells 21 of the stent 2. The stent further comprises a first side 2a which is an inside that faces an opening defined by the stent in which the valve leaflets are arranged. The struts 20 of the stent 2 are enclosed by the skirt 30, which forms a continuous wall that extends circumferentially in a peripheral direction of the stent 2.

According to the present invention, the implant 1 is produced by growing bacterial cellulose on the support structure 2 so that at least a part of the support structure 2, here the stent 2, is embedded in the bacterial cellulose of the functional element 3 to connect the functional element 3 (e.g. valve leaflets 31 and skirt 30) to the support structure/stent 2.

Optionally, after growing the bacterial cellulose, the implant can be treated with a solution of 2% by weight to 50% by weight of glycerol and/or 2% by weight to 50% by weight of a polyethylene glycol. The solution or solutions comprising glycerol and/or polyethylene glycol are preferably aqueous solutions. Preferably, the bacterial cellulose is then dried. Bacterial cellulose, in particular bacterial cellulose from *Acetobacter xylinum* that has been thus treated is now storable, since the bacterial cellulose is no longer brittle. The cellulose can now be processed and stored in the dry state without losing the mechanical characteristics of the material. It was also shown for example that the anti-inflammatory properties and good biocompatibility are retained. More details as to how the bacterial cellulose can be treated are to be found in published patent application No. US 2017/0312398 A1 and its counterpart international patent application WO 2016/083351 A1. The documents also disclose further steps, such as washing steps, which can be used to process the bacterial cellulose after production of the functional element through growing of the bacterial cellulose.

Preferably, the thickness of different parts of the functional element varies depending of the function of the part of the functional element. For example in the case of a heart valve prosthesis, the skirt region of the functional element can be made thicker than the heart valve element (or parts of the heart valve element). A thicker bacterial cellulose of the skirt region leads to a higher swelling capability of that part of the functional element which allows providing a better seal against paravalvular leakage. It is possible to control the thickness of the bacterial cellulose produced in the method disclosed here by varying the thickness of the oxygen-permeable mold. In regions of reduced thickness of the oxygen-permeable mold, more oxygen diffuses to the boundary layer between the culture solution and the oxygen-permeable layer, with the result that the aerobic bacterial growth is increased in this region, and therefore bacterial cellulose is deposited there to an increased extent. The resulting bacterial cellulose layer is therefore thicker in the regions where the oxygen-permeable material of the mold is thinner. Conversely, a thicker oxygen-permeable layer leads to a thinner bacterial cellulose layer, due to decreased oxygen diffusion through the thicker silicone layer. Therefore, it is possible to control the thickness of the bacterial cellulose layer by varying the thickness of the oxygen-permeable layer of the mold. This principle is illustrated in FIG. 3.

Figure 3:
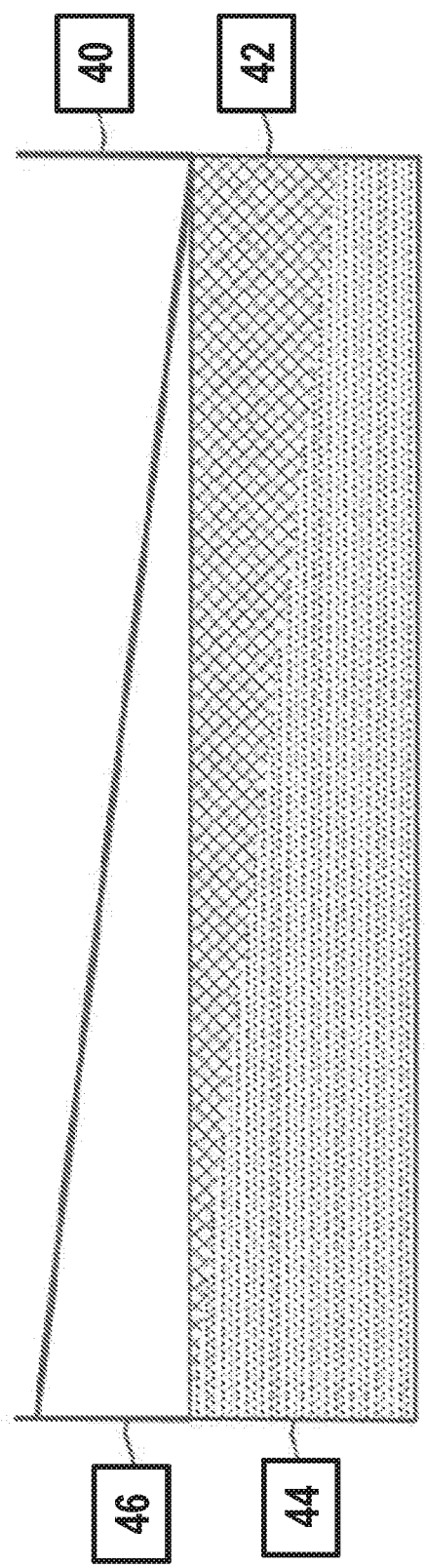
FIG. 3 shows a schematic depiction of a culture vessel, with which bacterial cellulose having different thicknesses can be generated by varying the thickness of the oxygen-permeable molding.

FIG. 3 presents a schematic illustration of a culture vessel 40, which is suitable for producing bacterial cellulose layers 42 having different thicknesses. According to one embodiment, 150 ml of a Hestrin/Schramm nutritive solution 44 are placed in the flat culture vessel 40 and are inoculated with 4 ml of an inoculation medium (for example *Acetobacter xylinum*). The culture vessel 40 is covered with a gas-permeable silicone membrane 46 in such a way that the only oxygen that can enter the vessel is the oxygen that diffuses through the oxygen-permeable membrane 46. The culture vessel 40 is placed in an oxygen-containing atmosphere in order to promote the aerobic growth of the bacteria on the silicone membrane 46. During incubation at 30° C. for several days, a cellulose layer 42 becomes deposited, which has the greatest layer thickness at the point where the silicone membrane 46 is the thinnest. Depending on the layer thickness of the silicone membrane 46 and the incubation period, layer thicknesses of the cellulose layer 42 in the range of 0.5 to 10 mm or more can be generated.

Bacterial cellulose which is to be used for medical implants calls for a high standard in terms of purity, particularly related to pyrogenic molecules. The layers of bacterial cellulose can contain residual bacteria, which may not be efficiently removed by conventional methods such as washing in aqueous alkaline solution (DE 40 27 479 A1, U.S. Pat. No. 4,588,400 A) and use of detergents, such as sodium dodecyl sulphate (SDS, EP 1 660 670 A). Therefore, in a preferred embodiment the first step i) of the inventive method comprises the sub-steps of:

a) transferring the body of bacterial cellulose into an aqueous solution of 1-10% by weight of at least one surfactant and 0.4-4% by weight of at least one base, b) treating the body of bacterial cellulose by means of microwaves at a temperature of at least 40° C., but less than 100° C., for 30-60 min, and c) washing the body of bacterial cellulose in a solution of aqueous weak acid in combination with application of microwaves, and rinsing with water.

EXAMPLES

In the following four different examples of basic technical processes for suturelessly connecting bacterial cellulose to an e.g. alloplastic support structure 2 (here stents) will be described.

Generally, bacteria from the classes of *Acetobacter xylinum* are able to produce bacterial cellulose in a nutrient solution given sufficient growing conditions which are for example known from Jia et al (Preparation and Characterization of Bacterial Cellulose Tube; DOI: 10.1109/ICBBE.2009.5163226). Particularly, the growth of bacterial cellulose does not take place in the entire volume, but only at an interface with an atmosphere containing oxygen. This characteristic can be used to form bodies or functional elements out of bacterial cellulose.

A typical nutrient solution or medium for bacterial cellulose producing bacteria (e.g. *Acetobacter xylinum*) that can be used in the framework of the present invention is given by: 20 g/l glucose, 5 g/l peptone, 5 g/l yeast extract, 2.7 g/l disodium hydrogen phosphate, and 1.5 g citric acid. This nutrient medium is inoculated with *Acetobacter xylinum*. In this nutrient medium, the bacterial cellulose is formed at typically 26-30° C. in an incubator over a period of 6 to 10 days. Other nutrient solutions may also be employed.

The functional elements with three-dimensional shapes can be generated with the following processes. They can assume any three-dimensional geometry. In general, the processes can be applied to any implant with an alloplastic support structure 2 and a functional element.

Optionally, the bacterial cellulose can be cut by 3D laser cutting with a $CO_2$ laser. Dried cellulose must first be rehydrated before cutting. This cutting step is for example important in order to separate the heart valve leaflets from each other at the commissures.

Several examples of how a heart valve prosthesis can be produced according to the method disclosed here are given below. It should however be understood that these methods can also be used to produce other types of implants than heart valve prostheses.

Example 1

Particularly, the method of Example 1 can be used, by way of example, to suturelessly connect a three-dimensional shaped functional element 3 comprising three valve leaflets 31 and an integral skirt 30 (e.g. of a TAVI heart valve prosthesis 1) to a support structure 2, which in this example is a stent.

Figure 1:
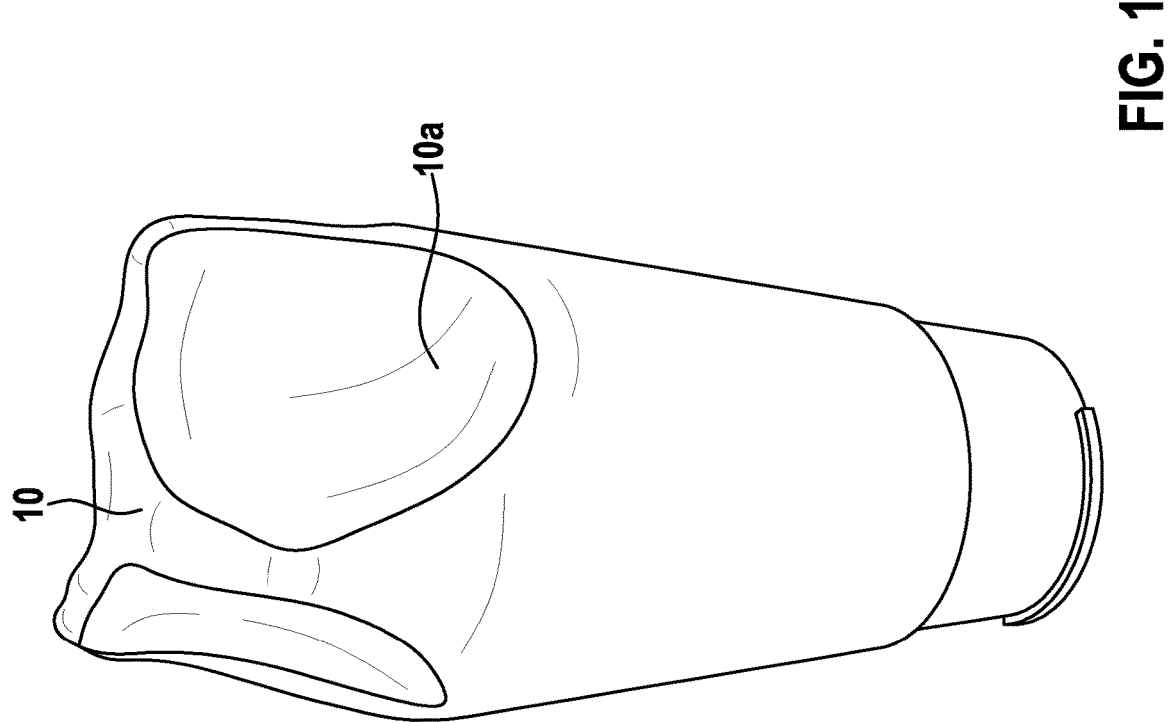
FIG. 1 is a perspective view of a first mold to form a heart valve element out of bacterial cellulose that is to be attached to a stent.

In a first step, a three-dimensional mold 10 (cf. FIG. 1) that is open to one side is produced in the desired shape, from a gas-permeable polymer such as silicone. The material thickness of the silicone can be in the range of 0.1 mm to 3 mm in order to achieve sufficient dimensional stability with sufficient oxygen permeability. The production of the mold is possible, for example, by means of a duplicating silicone, which is poured into a 3D-printed mold and cured. Alternatively, the silicone mold 10 is reproduced by multiple immersions of a 3D printed base form in the duplicating silicone. FIG. 1 shows such a molding 10 for the TAVI flap 30, 31 on the underlying 3D printed base form. The lower cylindrical symmetric part in the area of the skirt 30 is slightly smaller in diameter than the inner diameter of the stent 2 in the expanded state shown in FIG. 2. The upper part has the geometric shape of the valve leaflets 31 and is closed.

In a second step, a typical nutrient solution (also denoted culture medium) for bacterial cellulose producing bacteria (e.g. *Acetobacter xylinum*) is produced, which can be composed as described above. The nutrient solution is placed in a vessel that is open at the top.

In a third step, the stent 2 is placed on its side with the small diameter (lower side in FIG. 2) facing upward and the thin-walled silicone molded part (i.e. the first mold 10 shown in FIG. 1) is positioned with the open side facing upward in the lumen of the stent 2, aligned with the struts 20 of the stent. The two elements are then mechanically fixed relative to each other. The gap between the inside 2a of the stent 2 and the silicone mold 10 preferably lies between 0.05 mm and 1 mm according to an embodiment of the present invention in order to ensure stable growth of bacterial cellulose so as to embed a part of the stent 2.

In a fourth step, the unit consisting of the stent 2 and the silicone first mold 10 is immersed into the nutrient solution inoculated with bacteria and the vessel is hermetically sealed around the first mold 10. The only source of oxygen for the bacteria to deposit (grow) bacterial cellulose is that provided through the silicone mold 10. As a result, the bacterial cellulose functional element grows only on the outer surface of the mold 10a towards the stent 2. The bacterial cellulose is typically formed when the bacteria are incubated at 26-30° C. During the incubation, the bacterial cellulose grows on the mold and thus forms the functional element 3 including the valve leaflets 31 and a part of the functional element embeds a part of the stent. The thickness of the cellulose produced in 6 to 8 days lies in the range up to 2 mm.

At the end of the growth period, the first mold 10 is covered with bacterial cellulose on the surface 10a of the silicone first mold 10 and is attached to the stent 2 with sufficient mechanical stability for manual handling.

Further optional steps can be performed to increase the mechanical stability of the implant or to ready the implant for implantation. These further steps can also be performed in the methods of examples 2 to 4.

In order to increase mechanical stability, a fifth step can be conducted to further connect the bacterial cellulose to the struts 20 of the stent 2.

For this purpose, the unit consisting of the stent 2, the bacterial cellulose 3 and the first mold is removed from the nutrient solution and the first mold 10 is optionally removed.

The formed bacterial cellulose is sufficiently stable that this is possible manually. Subsequently, the inside of the bacterial cellulose 3 is filled with a new nutrient solution (e.g. composed as described above) and/or the outer surface is briefly immersed in the nutrient solution or poured over with the nutrient solution. This ensures that the bacteria present in the bacterial cellulose produced remain active and allows the bacterial cellulose to grow further in the presence of oxygen. The dipping or brief immersion may be performed several times. Over the course of several days, the close fit between bacterial cellulose and the e.g. alloplastic support structure 2 is increased. At the end of the growth phase, the resulting implant 1 can be rinsed in water and peripheral bacterial cellulose can be removed manually.

The bacterial cellulose can then be purified in a sixth step, in order to remove the endotoxins contained in the bacterial cellulose. A typical process that reliably removes endotoxins from the entire material is washing in 0.1 M sodium hydroxide solution at 80° C. for 72 hours followed by extensive rinsing steps in water and final steam sterilization at 121° C. for 20 minutes. Other methods for removing endotoxins are also possible.

The bacterial cellulose in this washed and moist form has a thickness of about 2 to 4 mm. Optionally, it is possible to dry the cellulose in a subsequent process step. This is possible by air drying or drying in the heating cabinet at 60° C. For this purpose, the implant 1 can be placed on a suitable, e.g. 3D-printed inner form in order to maintain a geometric shape of the valve leaflets 31. The thickness is reduced significantly to a maximum of 0.3 mm. After drying, the bacterial cellulose 3 is practically non-swellable and permanently dimensionally stable.

In order to obtain a swellable bacterial cellulose 3, it can be conserved by structure-stabilizing substances before drying, similar to the processes in dry conserved pericardium.

In a seventh step, the bacterial cellulose 3 on the implant 1 can be cut with a $CO_2$ laser by 3D laser cutting on a shaped body. This can for example be done to separate the valve leaflets 31 from each other along the commissures or to remove excess material. Dried cellulose must first be rehydrated. After the laser cutting, excess bacterial cellulose can be manually removed and the implant 1 can be washed, for example with water.

The implant 1 resulting from the described process consisting of an alloplastic support framework (nitinol) and a seamlessly bonded bacterial cellulose heart valve element, is shown in FIG. 2.

Further variations of the method for producing implants according to the invention are disclosed in the following examples. Other variations than those described here are possible.

Example 2

Figure 4:
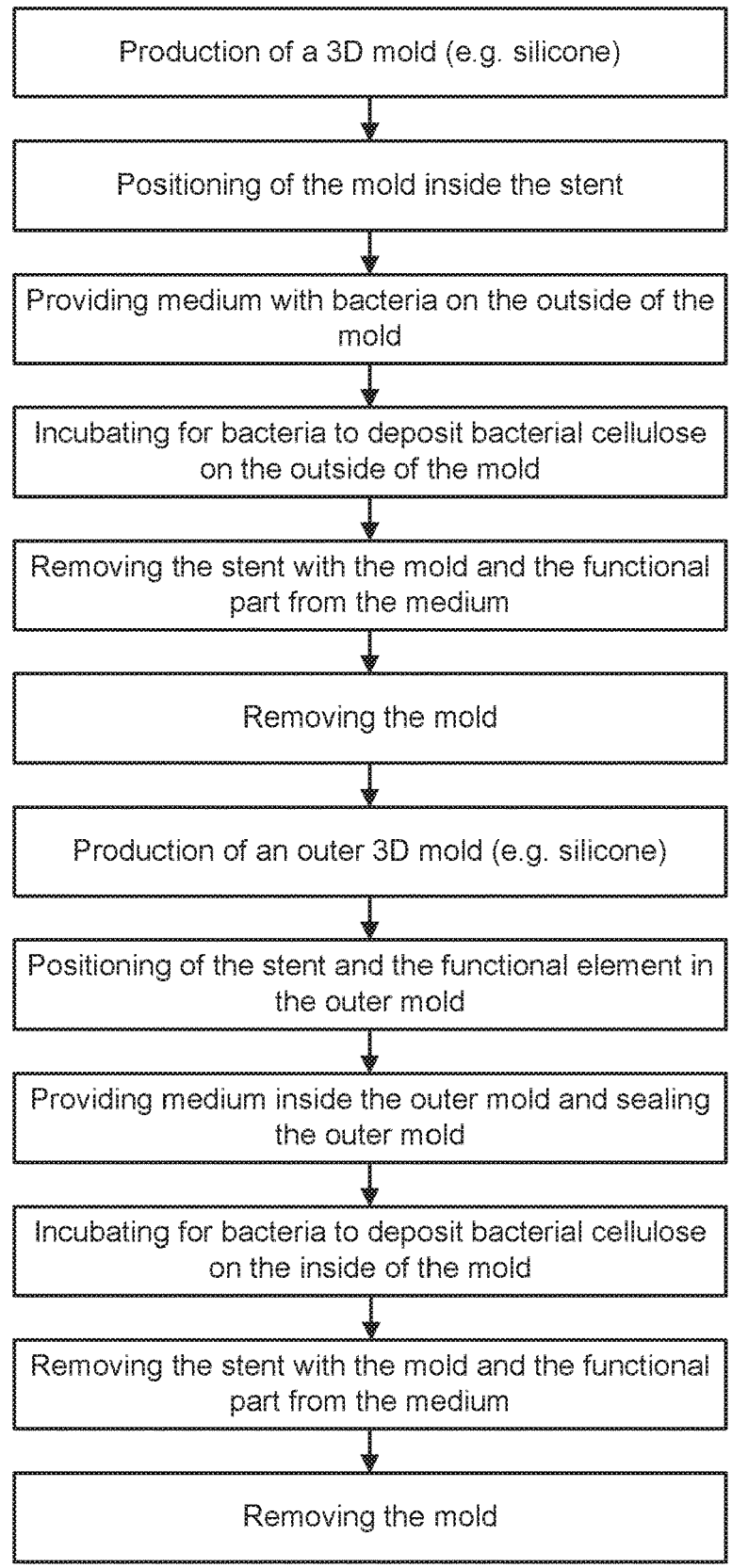
FIG. 4 schematically lists the steps of one embodiment of the method according to the invention.

The process is summarized in FIG. 4. Here, an oxygen permeable first (inner) mold (e.g. a silicone mold) is provided, and the first mold is arranged in the desired position relative to the stent 2, specifically in the opening 2c surrounded by the stent 2 (cf. e.g. FIG. 2). Furthermore, the nutrient solution with the bacteria is applied to the outside of the first mold in an airtight fashion. The only oxygen that is permitted to reach the bacteria is the oxygen that enters through the oxygen permeable mold. The bacterial cellulose therefore only grows on the mold. The bacterial cellulose is allowed to grow on the inside 2a of the stent 2 until part of the stent is embedded in the bacterial cellulose. Then, the stent 2 with the functional element 3 made of bacterial cellulose is removed from the first mold and the nutrient solution and is cleaned. Afterwards an oxygen permeable second (outer) mold (e.g. a silicone mold) is provided and arranged outside of the stent 2. Nutrient solution is applied to the second mold under airtight conditions and the bacterial cellulose is again allowed to grow on the outside 2b of the stent 2. The second bacterial cellulose layer thus grown allows providing a thicker outer skirt and a stronger connection between the bacterial cellulose and the stent. Again, the second mold and the nutrient solution are removed, and the stent and functional element connected thereto can be cleaned.

Example 3

In this example the two bacterial cellulose parts are grown in the reverse order as compared to example 2.

Here, an oxygen permeable first (outer) mold (e.g. a silicone mold) is provided, and the stent 2 is connected to the first mold, wherein the first mold is arranged outside the stent 2 (cf. e.g. FIG. 2). Furthermore, the nutrient solution is applied to the first mold in an airtight fashion. Then, the bacterial cellulose is allowed to grow on the outside 2b of the stent 2. Then, the stent 2 is removed from the first mold and the nutrient solution and is cleaned. Afterwards an oxygen permeable second (inner) mold (e.g. a silicone mold) is provided and arranged inside the stent 2 (i.e. in opening 2c). Nutrient solution is again applied to the second mold under airtight conditions and the bacterial cellulose is again allowed to grow on the inside 2a of the stent 2 until the stent is properly embedded in the grown functional element 3. Again, the second mold and the nutrient solution are removed, and the stent and functional element connected thereto can be cleaned.

Example 4

In the previous examples, the mold(s) 10 used for growing the functional element 3 of the prosthesis have to be oxygen-permeable in order to allow growth of the bacterial cellulose in the positions where the mold 10 provides oxygen through its oxygen-permeable property. However, it is also possible to grow the functional element 3 with a mold that is not oxygen-permeable. This is achieved by repeated dipping of the mold 10 and the stent 2 in medium comprising the bacteria over the course of several days. As a result, the bacteria are able to grow bacterial cellulose on the mold 10 and on the stent 2 because oxygen is always present. Repeated dipping/immersion serves to replenish the nutrients required for the bacteria to continue to grow the bacterial cellulose.

In this alternative, an (optionally oxygen permeable) first (inner) mold is provided and the first mold is positioned within the stent 2 (e.g. in opening 2c) so that the first mold is spaced apart from the inside 2a of the stent 2.

Then the nutrient solution is transferred to the stent 2 and the first mold, e.g. by dipping the stent 2 and first mold 10 or alternately filling/emptying a vessel in which stent 2 and first mold are positioned. The bacterial cellulose thus grows directly on the first mold and on the stent. Thereafter, the nutrient solution and the first mold is removed from the stent 2 and the latter can be cleaned.

The invention claimed is:

1. An implant with a support structure and a functional element produced by a method comprising the following steps:
   a) providing the support structure, the support structure having a three-dimensional shape;
   b) providing a three-dimensional mold of the functional element;
   c) positioning the mold relative to the support structure;
   d) providing a medium comprising a bacterial cellulose-producing bacteria such that the medium contacts the mold and the support structure;
   e) subjecting the mold, the support structure, and the medium to bacterial cellulose-growing conditions to grow bacterial cellulose on, in, or on and in the mold (1) to form the functional element from the bacterial cellulose and (2) to embed at least a part of the support structure in at least a part of the bacterial cellulose of the functional element, thereby connecting the functional element to the support structure; and
   f) drying the bacterial cellulose at a temperature of from 40 to 70° C.,
   thereby forming the functional element comprised of non-swellable bacterial cellulose and having a three-dimensional shape that deviates at least in part from the three-dimensional shape of the support structure, wherein at least a part of the support structure is embedded in the functional element.

2. The implant according to claim 1, which further comprises a step of exposing the bacterial cellulose to at least one structure-stabilizing solution before step f).

3. The implant according to claim 1, further comprising a step of removing the mold after step e) and further growing the bacterial cellulose on the functional element, on at least a part of the support structure, or on the functional element and at least part of the support structure, in an absence of the mold.

4. The implant according to claim 1, which comprises growing the bacterial cellulose in step e) by incubating the support structure and a side of the mold facing the support structure in the medium comprising bacterial cellulose-producing bacteria.

5. The implant according to claim 4, wherein the cellulose-producing bacteria is *Acetobacter xylinum*.

6. The implant of claim 1 wherein after step e) the bacterial cellulose is washed.

7. The implant of claim 1 wherein in step f) the bacterial cellulose is dried at a temperature of 60° C.

8. The implant of claim 1, wherein the functional element formed in step e) has a thickness of 0.5 to 10 mm.

9. The implant of claim 8, wherein the functional element formed in step e) has a thickness of 2 to 4 mm.

* * * * *